US007070817B2

(12) United States Patent
Kuppam

(10) Patent No.: US 7,070,817 B2
(45) Date of Patent: Jul. 4, 2006

(54) HERBAL COMPOSITION FOR TREATING OR ALLEVIATING VASCULAR HEADACHES, NEUROLOGICAL CONDITIONS AND NEURODEGENERATIVE DISEASES

(75) Inventor: Chandrasekhara Rao Kuppam, Hyderabad (IN)

(73) Assignee: Murali K Chada, Hyderabad (IN)

( * ) Notice: Subject to any disclaimer, the term of this patent is extended or adjusted under 35 U.S.C. 154(b) by 223 days.

(21) Appl. No.: 10/180,264

(22) Filed: Jun. 26, 2002

(65) Prior Publication Data
US 2004/0001896 A1    Jan. 1, 2004

(51) Int. Cl.
*A61K 9/48*    (2006.01)
*A61K 9/20*    (2006.01)
*A61K 35/78*   (2006.01)
*A61N 65/00*   (2006.01)

(52) U.S. Cl. .............. 424/734; 424/451; 424/452; 424/464; 424/465; 424/725; 424/751; 424/769

(58) Field of Classification Search ............... 424/725, 424/774, 769, 734, 751, 451, 464, 452, 465
See application file for complete search history.

(56) References Cited

U.S. PATENT DOCUMENTS

| 4,857,325 | A | * | 8/1989 | Albeck et al. ............... 424/754 |
| 4,976,960 | A | * | 12/1990 | Grossman et al. .......... 424/750 |
| 4,986,985 | A | * | 1/1991 | Grossman et al. ..... 424/195.17 |
| 5,276,043 | A |   | 1/1994 | Lippiello |
| 5,536,506 | A |   | 7/1996 | Majeed |
| 5,693,327 | A |   | 12/1997 | Shah |
| 6,365,601 | B1 | * | 4/2002 | Gaikar et al. ............... 514/315 |
| 6,383,495 | B1 |   | 5/2002 | Ramakrishna |
| 6,500,470 | B1 |   | 12/2002 | Pauly |
| 6,780,441 | B1 |   | 1/2003 | Solanki |
| 6,573,299 | B1 | * | 6/2003 | Petrus ........................ 514/558 |
| 6,582,733 | B1 |   | 6/2003 | Pruthi |
| 6,667,047 | B1 |   | 12/2003 | Brown |
| 6,730,332 | B1 | * | 5/2004 | Agarwal et al. ............ 424/769 |
| 6,855,347 | B1 | * | 2/2005 | Rao et al. ................... 424/734 |

FOREIGN PATENT DOCUMENTS

WO    PCT/US99/11785    12/1999

OTHER PUBLICATIONS

Sardi "A New Look at Eye Health" "Nutrition Science News" Apr. 2001 p. 1-8.*
Foidl et al "The Potential of Moringa Oleifera", Dar Es Salaam Oct. 20-Nov. 2, 2001 20 pages.*
"Herbal Monograph" The Himalaya Drug Company "Moringa" 2002 pp. 1-3.*

* cited by examiner

*Primary Examiner*—Herbert J. Lilling

(57) ABSTRACT

The invention relates to an herbal composition comprising extract of plant *Moringa Oleifera*, a member of family Moringaceae, plant *Piper Nigrum*, a member of family Piperaceae and plant *Nicotiana Tabacum*, a member of family Solanaceae for treating or alleviating of vascular headaches, neurological conditions and neurodegenerative diseases. The invention also reveals a method of preparing and using the composition.

7 Claims, No Drawings

HERBAL COMPOSITION FOR TREATING OR ALLEVIATING VASCULAR HEADACHES, NEUROLOGICAL CONDITIONS AND NEURODEGENERATIVE DISEASES

FEDERALLY SPONSORED RESEARCH

Not Applicable

SEQUENCE LISTING PROGRAM

Not Applicable

BACKGROUND

1. Field of Invention

This invention relates to compositions made from plants extract and method for treating or alleviating vascular headaches, neurological conditions and neurodegenerative diseases. More particularly, it relates to a composition comprising of plants *Moringa Oleifera, Piper Nigrum, Nicotiana Tabacum* and a pharmacologically acceptable carrier for treating Migraine, Parkinson's disease, Alzheimer's disease, Glaucoma, Epilepsy, Chronic depression and other conditions indicated by vasodilation, neuronal cell death and altered electrical activity in the brain.

BACKGROUND

2. Description of Prior Art

On an average, 26 million Americans, out of which 70% are women, suffer from migraine. Migraine headaches are a recurrent, throbbing headache generally felt on one side of the head, which usually begins in early childhood or in adolescent life. Migraines are caused by rapid dilation and constriction of blood vessels in the brain. This leads to increased pressure on the pain fibers in the blood vessel wall leading to severe headache. The most common triggering factors of migraine are hunger, extreme changes in weather, fatigue, emotional stress and oral contraceptives.

Although there are various factors that trigger migraine in any particular patient, researchers and physicians believe that migraine is finally a neurobiological disorder involving one or more overlapping neurobiological mechanisms. The pathophysiology of migraine involves both the Central Nervous System (CNS) and peripheral pathways. The peripheral pathways involve blood vessels and the CNS pathways involve the cortex, raphae nuclei and trigeminal caudate nucleus. It is observed that migraine headaches begin in the cortex region of the brain with possible changes in electrical activity. This descends to the brain stem region, which has maximum serotonergic projections. Trigeminal caudate nucleus, which is a brain stem region, is an important center for headaches and is affected in migraine headache. The activation of trigeminal sensory nerve fibers leads to a painful neurogenic inflammation within the meningeal vasculature. This results in the release of neuropeptides from trigeminal sensory fibers characterized by vasodilatation and plasma protein extravasation. Thus, although alterations in blood vessels are manifested as the final common pathway, a cascade of events initiating from cortex and affecting various structures, involving different pathways and release of neurotransmitters are seen in the brain.

The level of serotonin in the blood alters at the onset of headache and is normal between migraine attacks. Serotonin is a neurotransmitter present in the central nervous system and is normally inhibitory in function. It suppresses nerve signals in neurons and is commonly known as 5-HT (5-Hydroxytryptan). Migraine can be precipitated by the drug reserpine, which depletes serotonin and is relieved by serotonin agonists that combine with the receptors and simulate serotonin activity. In the vascular tissue, it is known that sumatriptan and other triptan drugs cause constriction of blood vessels in the cerebral region and reverses neurogenic inflammation around blood vessels during migraine attacks.

In spite of considerable research into causes and treatment of migraine, cure for this disease has eluded scientists. Among the various medications that are available the family of drugs called triptans are the most effective. The basic mode of action of all these triptan drugs is known to involve selective activation of certain serotonin receptor subtypes, primarily 5HT-1B receptors present on blood vessels and 5HT-1D receptors which are seen on the nerve cell terminals in both peripheral and central nervous system. Triptans are known to relieve migraine headache by constricting the swollen cranial blood vessels and thereby reducing pain. However, it is known that the blood-brain barrier opens during migraine allowing the triptans to enter the brain and thereby exposing the neurons to adverse reactions.

Though triptans are widely used for migraine, they do not work well for all patients. It is known that triptans do not work well in 20–25% of the patients and fail 40% of the time in patients who have earlier responded well to this class of drugs. The other disadvantages of present medication prescribed for migraine headaches are:

1) Simple analgesics used for headache cannot cure migraine in particular. Addiction to these medicines can lead to gastric ulcers 2) Repeated triptan intake leads to recurrent and chronic headaches 3) Triptan drugs have major side effects like cardiovascular problems, hypertension and even stroke.

4) Other common side effects are head, jaw, chest and arm discomfort and their tightening or tingling. Throat discomfort, muscle cramps and flushing are also seen.

The drawbacks in the treatment, and deficiencies in understanding Migraine has also been shown in U.S. Pat. No. 6,068,999. And, considering the number of people suffering from this disease there is an urgent need for a safe and effective treatment for migraine.

Alzheimer's disease is one of the most complex and perplexing neurodegenerative diseases characterized by memory loss, deterioration of language skills, impaired visuospatial skills, poor judgment, indifferent attitude, but preserved motor function. Basal forebrain and cholinergic systems are the principal targets in this disease. Patients suffer from a progressive performance degradation of visual recognition and memory.

No cure for Alzheimer's disease is currently available and no treatment can stop its advancement. In the early and middle stages of the disease drugs like tacrine, donepezil, rivastigmine, etc may help to prevent the symptoms from aggravating for a limited period of time. All these drugs have side effects. Tacrine may cause nausea, vomiting, diarrhea, abdominal pain, skin rash and can also damage the liver. Donepezil's side effects include nausea, vomiting, diarrhea, insomnia and anorexia.

Present day therapies focus on treating the associated symptoms like depression, agitation, sleep disorders, hallucinations and delusions. Addition of precursors like choline, lecithin and muscuranic agonists have proved ineffective.

Alzheimer's disease is being actively researched. A number of new drugs are being tested to see if they prevent or slow the disease.

Parkinson's disease is another common neurodegenerative disease found in the elderly population. About 50,000 new cases of this disease are reported in USA alone. Major clinical manifestations of this disease are bradekinesia (difficulty in voluntary movements), rigidity, body tremors, postural instability and impaired balance. This disease is marked by loss of pigmented neurons in the substantia nigra in the mid brain region. Dopamine neurons in the substantia nigra and other catecholamine neurons in the brainstem are selectively lost in this condition. The cause of cell death or impairment is not known.

Parkinson's disease cannot be cured at present. Medication is available to provide relief from the symptoms. There are two general approaches to the treatment of Parkinson's disease with medication. The first approach attempts to slow the loss of dopamine in the brain and the second approach attempts to treat the symptoms of Parkinson's disease by other means. Dopamine agonists do carry a higher risk of short-term side effects such as nausea, vomiting, dizziness, light-headedness, confusion, and hallucinations. Anticholinergics are used to restore the balance between the two brain neurotransmitters dopamine and acetylcholine, by reducing the amount of acetylcholine. This reduces tremor and muscle stiffness in patients with Parkinson's. These medications, however, can impair memory and thinking, especially in older people; therefore, they are rarely used today.

Levadopa is the most widely used drug for Parkinson's disease though not all symptoms respond to it. It delays the onset of debilitating symptoms for some time. Levadopa is not without side effects. Nausea, vomiting, low blood pressure, involuntary movements and restlessness are seen in patients using this medication.

Trigeminal neuralgia affects the trigeminal nerve in the head. This nerve is responsible for sending impulses of touch, pain, pressure and temperature to the brain from the face. Though not fatal this disease is characterized by sudden stabbing pain felt on one side of the face. Another feature of this disorder is successive recurrences and remissions that may incapacitate the patient. Treatment for this condition includes anticonvulsant medicines such as carbamazepine or phenytoin. If this fails, surgical intervention is recommended.

Glaucoma is a major public health problem affecting about sixty six million people around the world. There are approximately three million patients in America alone. Glaucoma is an optic nerve degenerative disease that causes loss of vision and blindness. A characteristic feature of glaucoma is the progressive death of retinal ganglion cells. In many cases this is caused by the increased intraocular pressure, which leads to axonal degeneration in the optic nerve and loss of ganglion cells.

Early diagnosis is very important in the treatment of glaucoma. Though there is no cure to this disease it can be controlled to some extent with surgery and medication. Prolonged usage of drugs is required. Some medicines can cause headaches or have side effects on other parts of the body. There is an urgent need for new medicines that specifically arrest ganglion cell death.

As has been described above, diseases of the brain are generally incurable. All available treatments are symptomatic and relief is limited. Prolonged usage of drugs has variety adverse effects on the patients. Treatment often calls for surgical intervention. Invasive procedures are not free of risks. They have the potential to cause irreversible damage.

U.S. Pat. No. 6,405,079 while discussing the various shortfalls in treating neurological and other problems, offers yet another invasive procedure that may require permanent implantation of electrodes. U.S. Pat. No. 6,277,372 also suggests that there is a general lack of treatment for neurodegenerative diseases. It traces these diseases to defects in neural circuitry and offers a method of treating neurodegenerative diseases by transplanting porcine neural cells into a human subject. Such a method requires extremely advanced medical procedures and can be very expensive. And, as pointed out in that patent application, such treatment may be accompanied by administration of immunosuppressive drugs. Moreover, implantation of foreign neural matter as an accepted and safe course of treatment is debatable.

It is therefore the object of this invention to overcome the drawbacks described in the currently available treatments and provide a safe and natural composition to treat conditions affecting the neurological system.

OBJECTS AND ADVANTAGES

It has been shown above that available treatments for neurological conditions and diseases are not curative. Even drugs that have become available recently as a result of cutting edge research are deficient in this regard. Often surgical intervention is recommended for some conditions though surgery does not fully correct or cure those conditions. While surgery brings some benefit it must be understood that neurosurgery is not an entirely safe procedure. It can cause irreversible damage and lead to disruptive changes in the live style of the patients.

It is the object of this invention to provide a natural composition and method to treat vascular headaches, neurological conditions and neurodegenarative diseases.

A further object of the invention is to provide a treatment that is safe in prolonged usage.

Another object of the present invention is to provide a method of treatment that is non invasive and thereby reducing the suffering the patient has to endure.

Yet another object of this invention is to provide a composition and method of treatment that is easy to produce and practice.

SUMMARY

The present invention relates to an herbal composition and method for the treatment or alleviation of vascular headaches, neurological conditions and neurodegenerative diseases. In the preferred embodiment, the composition comprises of therapeutically active extract of *Moringa Oleifera, Piper Nigrum, Nicotiana Tabacum* and a pharmacologically acceptable carrier. Also, in the preferred embodiment, the composition is administered on the subjects in need of such treatment as eye drops.

The list of neurological conditions and diseases that can be treated with the present invention include specific conditions like migraine, cluster headaches, parkinson's disease, alzheimer's disease, trigeminal neuralgia, glaucoma and epilepsy. Apart for these, the present invention is found to be very useful in treating most conditions that are generally indicated by vasodilatation, altered neuronal activity, neural degeneration, neuralgias and alteration in levels of neurotransmitters.

The present invention comprises of natural plant based ingredients that have been used as food or spice in India and other parts of the world. Though *Nicotiana Tabacum* is known to be carcinogenic in prolonged and habitual use, its extract used in small doses as described in the preferred embodiment, has shown therapeutic properties.

DETAILED DESCRIPTION

This invention relates to the use of a composition made from extract of plants for treating or alleviating vascular headaches, neurological conditions and neurodegenerative diseases. In the preferred embodiment, the composition comprises of therapeutically active extract of *Moringa Oleifera, Piper Nigrum, Nicotiana Tabacum* and a pharmacologically acceptable carrier.

*Moringa Oleifera*, sometimes referred to as *Moringa Pterygosperma* and commonly known as drumstick tree in English, Sajhna in Hindi, belongs to the Moringaceae family with 14 known species. *Moringa Olifera* is the most widely known and a plant native to India. It is also indigenous to some countries in Africa, Arabia, Asia and other regions. The *moringa* tree grows to a height of 5–12 meters, has evergreen or deciduous foliage with leaflets 1–2 centimeters in diameter and white or creamy colored flowers. The fruit (pod) grow up to 120 centimeters and is green in color.

A lot of research is focused on the antibiotic activity of the extract of this plant. The seeds and fruits have been shown to be useful in water purification. *Moringa* leaves are extremely nutritious and have a tremendous potential as a dietary supplement.

*Piper Nigrum*, commonly known as black pepper in English, Gol Mirch in Hindi belongs to the Piperaceae family. Black pepper is a tropical evergreen vine that is cultivated widely in India and South East Asia. The fruit when ripe is red. It is gathered before it is fully ripe and spread on mats in the sun, when it loses its red color and becomes black and shriveled. Black pepper is commonly used as a cooking spice and has been traditionally used in *Ayurveda* (India system of herbal medicine) as a treatment for: asthma, chronic indigestion, colon toxins, obesity, sinus congestion, intermittent fever, cold extremities, colic, cholera, gastric ailments, diarrhea, hemorrhoids, worms, sore throat.

*Nicotiana Tabacum*, commonly known as tobacco, belongs to the family Solanaceae. Of the many species of tobacco, *Nicotiana Tabacum* is grown throughout the world and is the main commercial crop used in manufacturing cigarettes.

*Moringa Oleifera, Piper Nigrum, Nicotiana Tabacum* have individually shown varying degree of therapeutic activity in alleviating neurological conditions. However, in the preferred embodiment of this invention the composition made from the extract of all the three plants has proved to be very efficacious in treating the said diseases and conditions. It should also be noted that various plant species belonging to the same genus group discussed in the invention could be used to make a composition that exhibit properties similar to the invention described here.

One of the major advantages of this invention is the ease with which the said composition can be prepared. A wide variety of techniques can be used to extract the therapeutically active ingredients from the plants. Though modern processes may have to be used for preparation of the composition for parenteral administration or for forms used in human medicine or for storage over extended period of time, age old methods of processing herbs can used as effectively. One such process is shown below.

The composition can be made using any parts of the plants or the whole plant, fresh or dried. In the preferred embodiment, fresh leaves of *Moringa Oleifera*, dried fruits of *Piper Nigrum* and dried leaves of *Nicotiana Tabacum* are used. Water is used as the carrier. The ingredients can be combined in any number of ways to get the desired effect. In the preferred embodiment, following are the approximate quantities of each ingredient:

| | |
|---|---|
| Moringa Oleifera | 140 grams |
| Piper Nigrum | 1.5 grams |
| Nicotiana Tabacum | 3.5 grams |
| Water | 400 ml |

Thoroughly clean freshly picked leaves of *Moringa Oleifera* to remove impurities and other foreign matter. Soak it in water for a few hours (soaking is optional). Separate the leaves from water and mechanically grind the leaves into a coarse paste. Add dried fruits of *Piper Nigrum* and dried leaves of *Nicotiana Tabacum* to the paste and grind it further into a fine paste. Water may be added to facilitate grinding the ingredients into a paste. Boil the mixture on low heat using the water it was soaked in or using fresh water till the volume of the resulting mixture reduces to about 100 ml. Allow the resulting liquid to cool. Using any acceptable filtering means to separate the particulate matter from the resulting solution.

The composition prepared as shown above or by any other means, can be administered to human and animal subjects orally or parenterally. It may be applied as eye drops or made into oral solutions, beverages, capsules or syrup. It can also be used as an injectable solution for intravenous, intramuscular or subcutaneous administration. The extract can be used topically by making ointments, lotions, sprays, etc.

The effect of the composition after administration both as eye drops and injections was studied on both human and animal subjects suffering from various neurological afflictions. The experimental observation could be summarized as below.

1) The experimental subjects were exposed to extreme environmental factors that are known to trigger migraine after application of the composition. These factors like extreme weather changes, fluorescent lights, strong odors, etc. failed to trigger the onset of migraine.

2) MRI study on migraine subjects has shown that after the application of the composition there is a reduction of dilatation of blood vessels in the brain.

3) The composition in this invention has been observed to mimic serotonin agonists like triptans.

4) Positron Emission Tomography (PET) was done on a small number of migraine subjects after the application of the said composition. It was observed that there was a decrease in regional cerebral blood flow (CBF) across the cortical surface and in the parietal and temporal lobes of the brain. The high CBF in these regions are known to be the common symptoms in headache conditions and also in alzheimer's disease.

5) Results with the composition treated subjects show significant changes in neuronal activity, which is an important factor in parkinson's disease and also in migraine.

6) The neuronal cell death is one of the most common causes for various neurodegenerative diseases like alzheimer's and glaucoma. The composition is known to reduce the cell death in the associated regions of specific diseases and hence has a therapeutic effect.

7) Depression is known to be a psychiatric condition involving neurobiological mechanisms. The composition serves as a medicine for such disease conditions also.
8) Application of the composition reduces the insensitivity and numbness of the face, attacks of severe pain and weakness of jaw muscles that are the characteristic symptoms of trigeminal neuralgia.

Conclusion, Ramifications and Scope of Invention

It has been established by experimental results that this invention is an effective treatment for various afflictions of the nervous system. Not only is the invention safe and easy to practice, it provides a superior alternative to existing treatments that involve expensive drugs, surgery or both. More importantly, the composition described in the preferred embodiment is free of serious adverse reactions that are caused by commonly used drugs. In summary, the composition was found to have therapeutic impact on various neurological conditions and its curative actions can be generally classified as below:

1) It reduces dilation of blood vessels
2) It acts similar to a serotonin agonist in cases of vascular headaches
3) It decreases cell death in neurodegenerative diseases
4) It restores the altered neuronal activity, which is characteristic of neurological disorders, to near normalcy
5) It brings down depression which is common in a few neurological conditions The description of this invention contains many specificities. These should not be construed as limitations to the scope of the invention, but rather an exemplification of the preferred embodiment. This invention can be varied in many ways without departing from the spirit and scope of the invention. For example, *Moringa Oleifera* may be replaced in the composition by any other species of the Moringaceae family (like *Moringa Concanensis Nimmo*) or, the ratios of the ingredients in the preferred embodiment may be varied over a very wide range by one skilled in art and yet arrive at a composition that works in a way similar to this invention.

Thus the scope of the invention should be determined by the appended claims and their legal equivalents, rather than by the examples given.

I claim:

1. An herbal composition for the treatment of vascular headaches, neurological disorders and neurodegenerative diseases, comprising:
    a therapeutically effective combination of extracts including;
    *Moringa Oleifera;*
    *Piper Nigrum;*
    *Nicotiana Tabacum;* and,
    a pharmaceutically acceptable carrier; wherein the extracts are obtained by boiling in water a ground mixture comprising of fresh leaves of the *Moringa Oleifera*, dried fruits of the *Piper Nigrum*, and dried leaves of the *Nicotiana Tabacum.*

2. The composition of claim 1, wherein the extracts include;
    a. between approximately 90–99% by weight of *Moringa Oleifera*
    b. between approximately 0.5–5% by weight of *Piper Nigrum*
    c. between approximately 0.5–10% by weight of *Nicotiana Tabacum.*

3. The composition of claim 1, wherein the composition is for the treatment of migraine headaches.

4. The composition of claim 1, wherein the composition is used for the treatment of neurological disorders and neurodegenerative diseases selected from the group consisting of;
    alzheimer's disease, parkinson's disease, glaucoma, epilepsy, trigeminal neuralgia, chronic depression, diseases characterized by neuronal degeneration, disorders characterized by altered neurological activity, disorders characterized by dilation of blood vessels in the brain, disorders characterized by depression and dementia.

5. The composition of claim 1, wherein the composition is formulated as tablets, capsules, eye drops, food supplements, liquids or tonics.

6. The composition of claim 1, wherein the composition is formulated for intramuscular, intravenous or subcutaneous administration.

7. The composition of claim 1, wherein the composition is formulated as a dispersible nasal or inhalant spray.

* * * * *